United States Patent
Schaeffer et al.

(10) Patent No.: US 6,220,243 B1
(45) Date of Patent: *Apr. 24, 2001

(54) INHALATION DEVICE

(75) Inventors: Alain Emile Edouard Schaeffer, Evreux; Etienne Seguelas, Chateau-Landon, both of (FR)

(73) Assignee: Laboratoire Glaxo Wellcome, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/494,942

(22) Filed: Feb. 1, 2000

Related U.S. Application Data

(63) Continuation of application No. 08/793,612, filed as application No. PCT/EP95/03603 on Sep. 13, 1995, now Pat. No. 6,065,471.

(30) Foreign Application Priority Data

Sep. 16, 1994 (GB) .................................................. 9418702
Apr. 13, 1995 (GB) .................................................. 9507713

(51) Int. Cl.[7] ......................... A61M 15/00; A61M 16/00; B05D 7/14; B05D 83/06
(52) U.S. Cl. .............................. 128/203.15; 128/203.12; 604/58
(58) Field of Search ........................ 128/200.14, 200.17, 128/203.12, 203.15, 203.23; 604/57, 58

(56) References Cited

U.S. PATENT DOCUMENTS

| | | |
|---|---|---|
| 2,470,296 | 5/1949 | Fields . |
| 2,470,297 | 5/1949 | Fields . |
| 2,534,636 | 12/1950 | Stim . |
| 2,587,215 | 2/1952 | Priestly . |
| 5,349,947 | 9/1994 | Newhouse et al. . |
| 5,355,873 | 10/1994 | Del Bon et al. . |
| 5,372,128 | 12/1994 | Haber et al. . |
| 5,394,868 | 3/1995 | Ambrosio et al. . |
| 5,437,270 | 8/1995 | Braithwaite . |
| 5,657,748 | 8/1997 | Braithwaite . |
| 5,687,710 | 11/1997 | Ambrosio et al. . |
| 5,740,792 | 4/1998 | Ashley et al. . |
| 5,829,434 | 11/1998 | Ambrosio et al. . |
| 5,975,076 * | 11/1999 | Yianneskis et al. ............. 128/203.15 |
| 6,065,471 * | 5/2000 | Schaeffer et al. ............... 128/203.15 |

FOREIGN PATENT DOCUMENTS

| | | |
|---|---|---|
| 9200771 | 1/1992 | (WO) . |
| 9414492 | 7/1994 | (WO) . |

* cited by examiner

*Primary Examiner*—Glenn K. Dawson
*Assistant Examiner*—Joseph Weiss, Jr.
(74) *Attorney, Agent, or Firm*—Bacon & Thomas

(57) ABSTRACT

An inhalation device is provided by means of which material in powder form can be inhaled. The device comprises a body 55 defining a reservoir 56 for medicaments in powder form, an outlet 57 through which a user can inhale and a dosing member 53 with at least one metering recess 65 formed therein. The dosing member 53 is moveable between a position in which the at least one metering recess 65 communicates with the reservoir 56 to receive a dose of powder therefrom and a position in which the at least one metering recess 65 communicates with the outlet 57 to permit the user to inhale the dose. The at least one metering recess 65 is formed in a face of the dosing member 53, the said face being mounted in contact against a similar mating face 60 of the body 55 at the lower end of the reservoir 56. At least one moveable weight may be incorporated within the device, adapted to strike an anvil surface when the device is shaken.

30 Claims, 7 Drawing Sheets

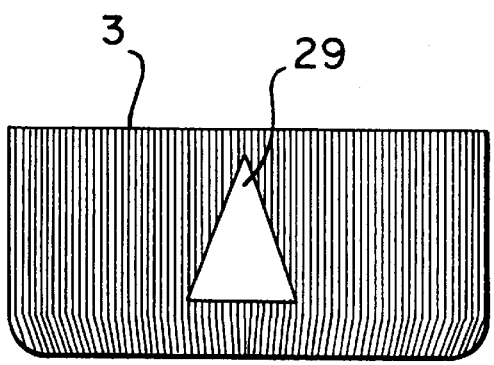
FIG. 10
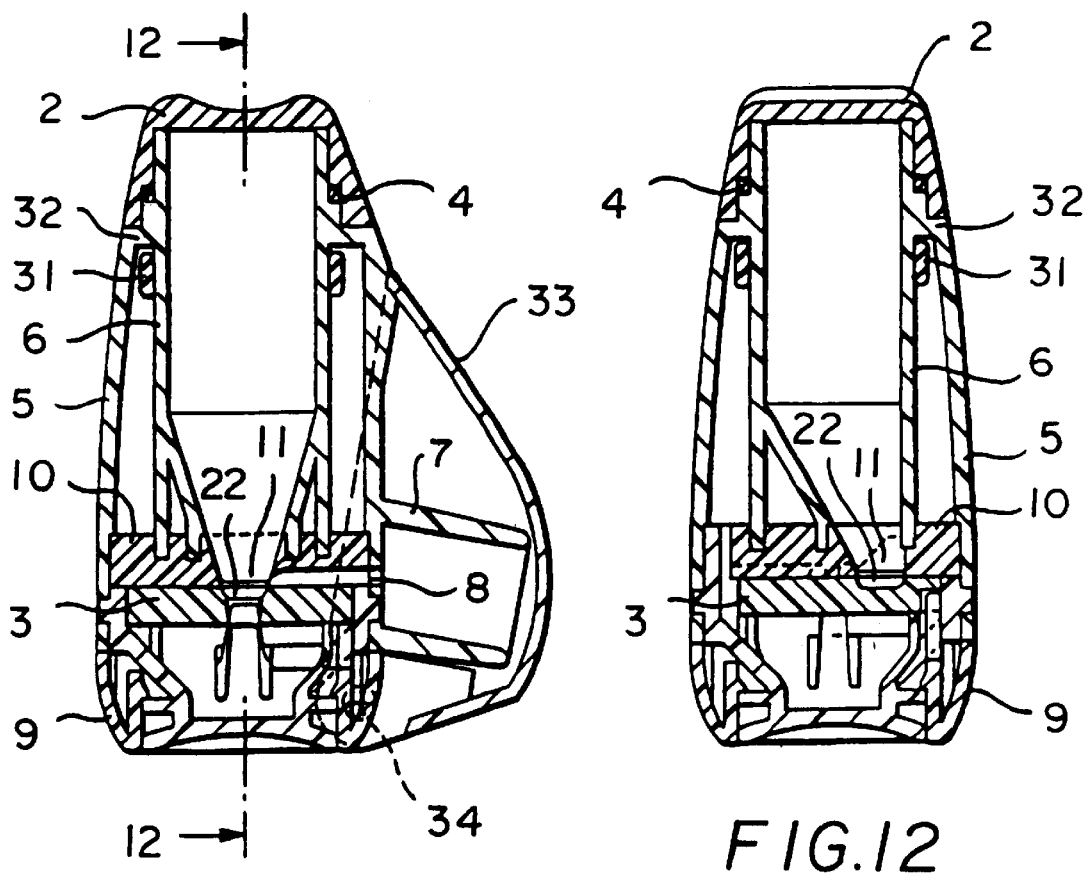
FIG. 11
FIG. 12

INHALATION DEVICE

This application is a continuation application of U.S. application Ser. No. 08/793,612 filed Jun. 17, 1997, now U.S. Pat. No. 6,065,471, which is a 371 of PCT/EP95/03603 filed Sep. 13, 1995.

This invention relates to an inhalation device by means of which metered doses of medicament in the form of a powder can be dispersed to a user. In particular it relates to a device of the type in which the medicament powder is held in bulk in a reservoir with which the device is provided, and is metered to the user from the reservoir.

In devices of the type just described, it is difficult to obtain doses which are equal to a nominal value to within the appropriate tolerance. It will be understood that the tolerance permitted is often very small, as it is important that the user should be given a dose which is very close to the nominal value. In order to maintain the medicament powder in a manageable state it needs to be kept dry. Any ingress of moisture into the reservoir from outside can cause the medicament powder to agglomerate and this may be detrimental to its free flowing properties rendering it difficult to meter consistent doses from the reservoir. In the absence of adequate reservoir sealing it may be necessary to incorporate a desiccant cartridge into the reservoir to absorb any moisture that does enter. This is often insufficient to prevent deterioration of the medicament powder.

It is an object of the present invention to provide a device of the type just described, in which doses can be repeatedly accurately dispersed, without requiring a dispensing mechanism of undue complexity.

It is a further object of the present invention to provide a device of the type just described, but which additionally incorporates a simple and efficient sealing means to prevent ingress of moisture into the reservoir.

According to the present invention there is provided an inhalation device comprising a body defining a reservoir for medicament in the form of a powder, an outlet through which a user can inhale, and a dosing member with at least one metering recess formed therein, the dosing member being moveable between a first position in which the at least one metering recess communicates with the reservoir to receive a dose of powder therefrom and a second position in which the at least one metering recess communicates with the outlet to permit the user to inhale the dose, the at least one metering recess being formed in a face of the dosing member, the said face being mounted in contact against a similar mating face of the body at the lower end of the reservoir, and at least one moveable weight adapted, when the device is shaken, to strike an anvil surface defined in the device.

The at least one weight may be slidable longitudinally of the device in a respective bore, with the anvil surface being at the lower end of the bore.

Alternatively the weight may be in the form of a ring encircling the device and slidable longitudinally thereof.

According to a further aspect of the invention the face of the dosing member and the mating face of the body are sealing faces with highly polished smooth surfaces which form a sliding seal which excludes substantially all air from the interface therebetween.

Suitably the sealing faces have a surface texture sufficiently smooth to have a roughness average value (Ra) of 0.5 microns or less, preferably 0.2 microns or less.

Suitably the sealing faces are flat. More suitably they have a flatness of 0.005 mm or less, preferably 0.003 mm or less.

Alternatively the sealing faces may be frusto-conical. The sealing faces may alternatively be cylindrical. In a further alternative the sealing faces may be spherical.

The sealing surfaces are suitably made of a hard rigid material such as acetal resins, ceramics or metals.

A further aspect of the invention provides an inhalation device comprising a reservoir for medicament in the form of a powder, an outlet through which a user can inhale, a metering means adapted to communicate with the reservoir to receive a dose of powder therefrom and with the outlet to permit the user to inhale the dose, and at least one weight moveable in the device and adapted, when the device is shaken, to strike an anvil surface defined in the device.

Additionally the invention provides an inhalation device comprising a body forming a reservoir for medicaments in the form of a powder, an outlet through which a user can inhale, and a dosing member with at least one metering recess formed therein, the dosing member being moveable between a position in which the at least one metering recess communicates with the reservoir to receive a dose of powder therefrom and a position in which the at least one metering recess communicates with the outlet to permit the user to inhale the dose, the at least one metering recess being formed in a face of the dosing member, the said face being mounted in contact against a similar mating face of the body, characterised in that the said face of the dosing member and the said mating face of the body have highly polished smooth surfaces which form a contacting face to face kinetic seal which excludes substantially all air from the interface. The term 'kinetic seal' in this context means a seal that can withstand relative movement of the two faces.

Another embodiment of the invention provides an inhalation device comprising a body defining a reservoir for medicament in the form of a powder, an outlet through which a user can inhale, and a dosing member with at least one metering recess formed therein, the dosing member being moveable between a first position in which the at least one metering recess communicates with the reservoir to receive a dose of powder therefrom and a second position in which the at least one metering recess communicates with the outlet to permit the user to inhale the dose, the at least one metering recess being formed in a face of the dosing member, the said face being mounted in contact against a similar mating face of the body at the lower end of the reservoir, characterised in that the said face of the dosing member and the said mating face of the body are sealing faces with highly polished surfaces which form a sliding seal which excludes substantially all air from the interface therebetween.

The invention is further described below with reference to the accompanying drawings in which:

FIG. 10 is a side elevation of the dosing member of FIGS. 7 and 8;

FIG. 11 is a section through a second embodiment of a device according to the invention;

FIG. 12 is a section on line 12—12 in FIG. 11; and

Figure 1:
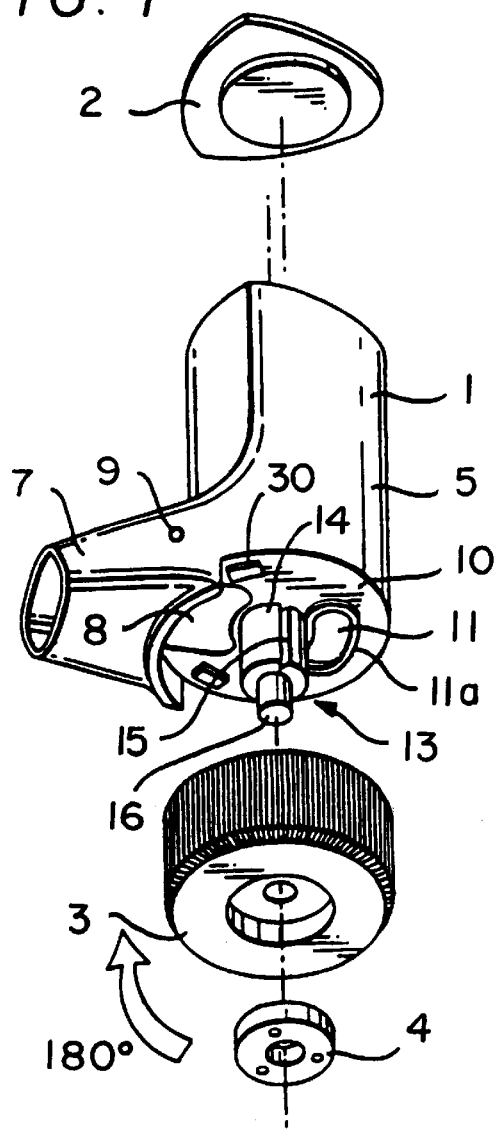
FIG. 1 is a perspective view of an embodiment of a device according to the invention, showing the main body components in disassembled form.
Figure 2:
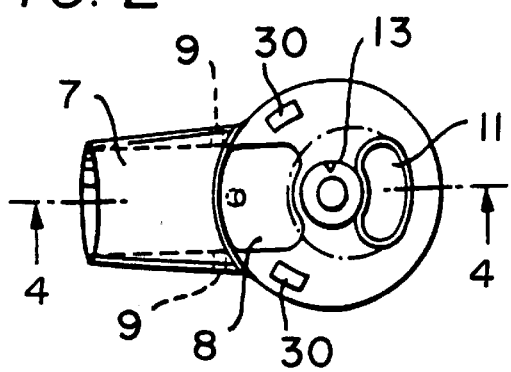
FIG. 2 is an underplan view of the body of the device of FIG. 1.
Figure 3:
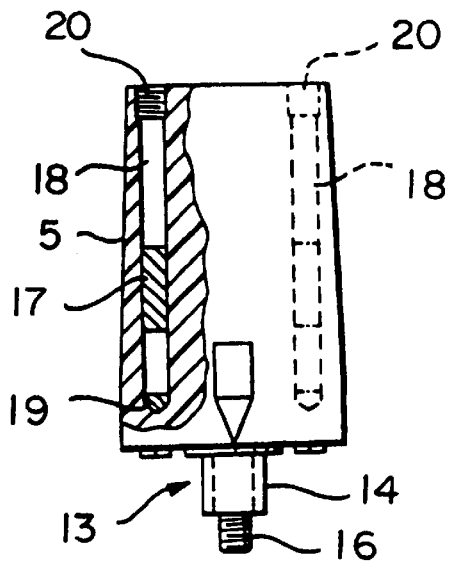
FIG. 3 is a rear view of the body, partly cut away.
Figure 4:
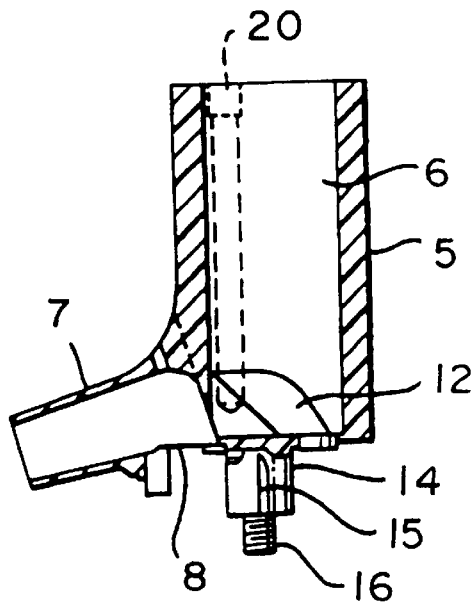
FIG. 4 is a section on line 4—4 in FIG. 2.
Figure 17:
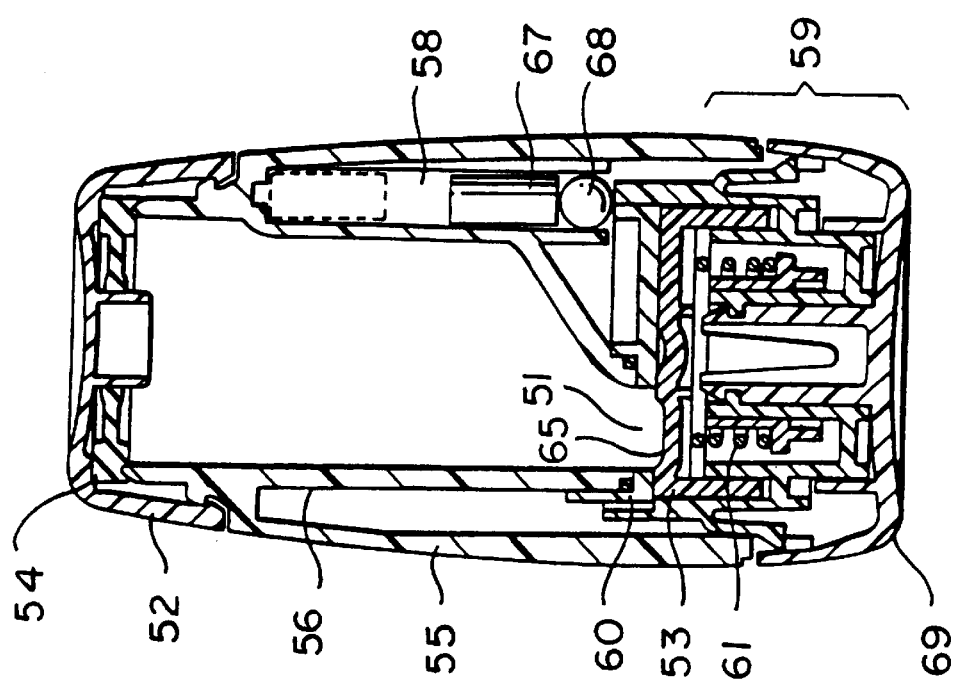
FIG. 17 is a section on line 17—17 in FIG. 16.
Figure 16:
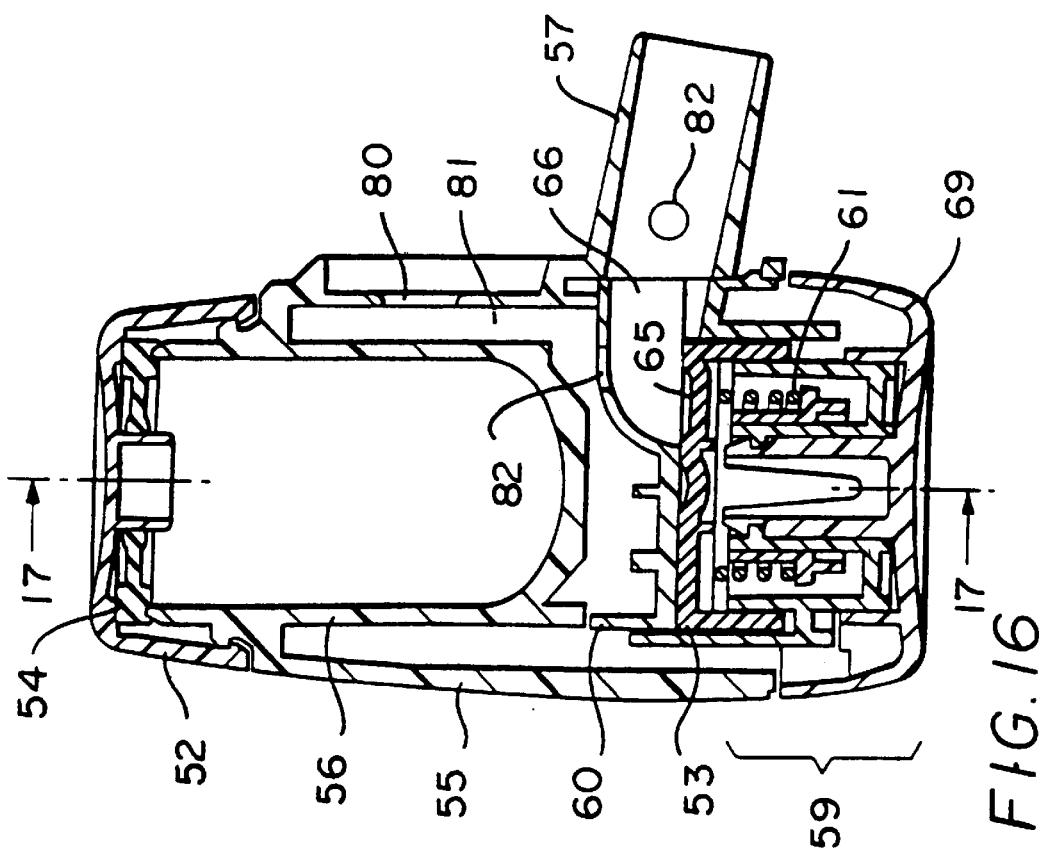
FIG. 16 is a section through a third embodiment of a device according to the invention.
Figure 18:
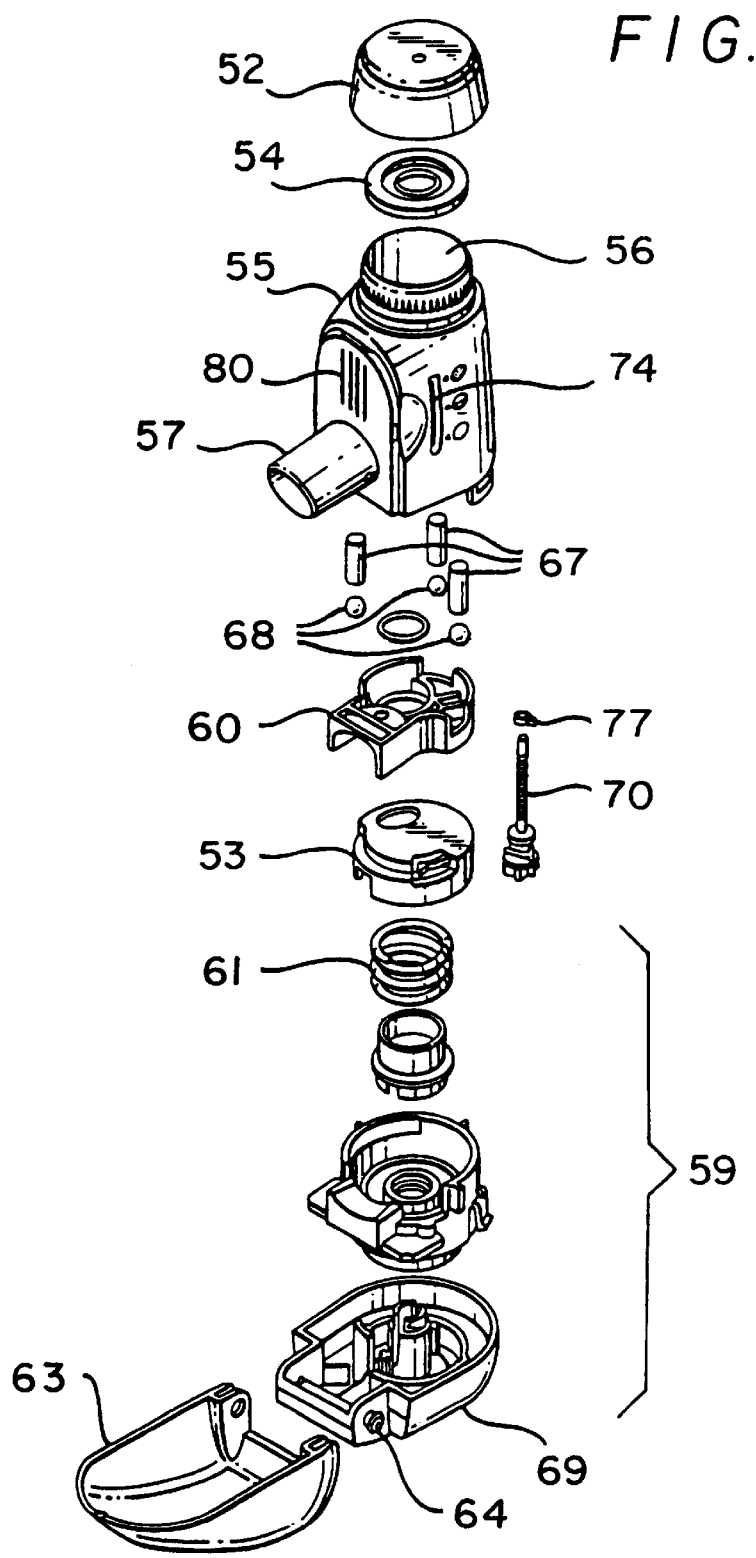
FIG. 18 is an exploded view of the embodiment shown in FIGS. 16 and 17.
Figure 19:
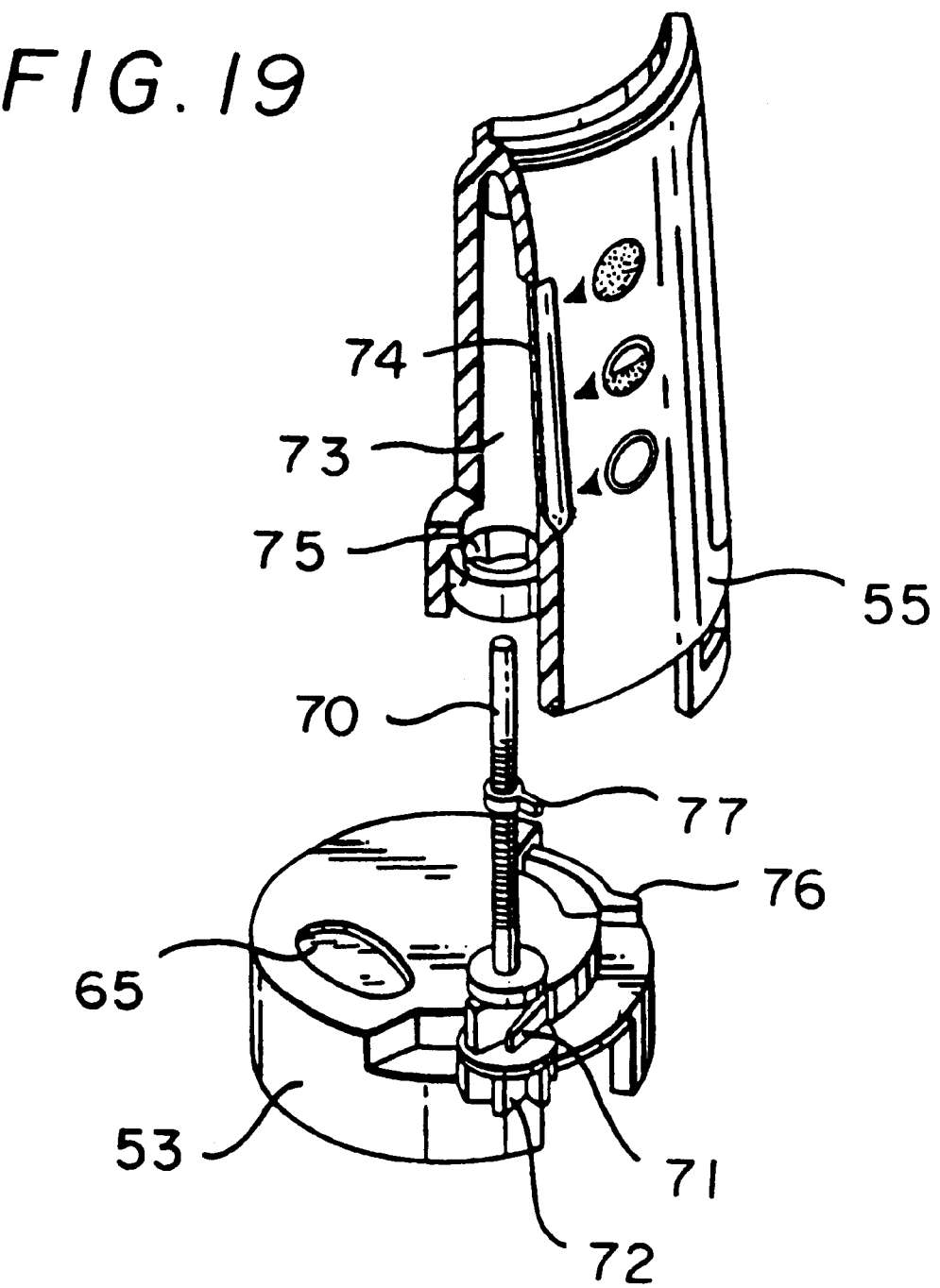

FIG. 19 is an exploded perspective view, partly cut away, showing the dose indicator mechanism of the embodiment shown in FIGS. 16 to 18, As shown in FIG. 1, the device comprises a body 1, a cover 2, a dosing member 3 and a nut 4. The body 1 has a elongate main body portion 5 which defines a reservoir 6. The body may be moulded from polycarbonate, aluminium or any other rigid material which will transmit vibrations. The reservoir 6 contains a supply of medicament in the form of a powder. As is common in powder inhaler devices of this type, the reservoir 6 may contain an overfill of powder to ensure that there is sufficient powder in the reservoir to deliver the correct dosage of powder for each of the prescribed number of doses for the powder supply contained. Thus, whilst the device may be provided with a prescribed life of 200 doses of powder, the reservoir may contain the equivalent of 240 doses of powder. The reservoir 6 may also be provided with a window (not shown) to allow the user to check whether there is sufficient powder remaining.

The medicament is one which is suitable for inhalation, and many such medicaments are well known to those skilled in the art, for example for the treatment of asthma. Powdered medicaments suitable for this purpose include salbutamol, beclomethasone, salmeterol, fluticasone, formoterol, terbutaline, budesonide and flunisolide, and physiologically acceptable salts, solvates and esters or any combination thereof. Preferred medicaments are salbutamol, salbutamol sulphate, salmeterol, salmeterol xinafoate, fluticasone propionate, beclomethasone dipropionate and terbutaline sulphate. Individual isomers, such as R-salbutamol, can also be used. It is to be understood that the medicament powder may consist purely of one or more active ingredients, or there may additionally be a carrier, for example lactose powder.

The upper end of the reservoir is closed by the cover 2 which may, for example, be provided with a desiccant cartridge (not shown) to absorb moisture and reduce the risk of the powder in the reservoir absorbing moisture and undergoing agglomeration of the particles thereof. The cover 2 may be removably secured to the body 1 by any known means, for example by means of a screw thread or a snap fit, to enable refilling of the reservoir 6 with powder. In this case a pharmaceutical grade rubber sealing ring (not shown) may be incorporated between the cover 2 and body 1 to prevent ingression of moisture into the reservoir 6. Alternatively, the device may be intended to be disposable after exhaustion of the supply of powder in the reservoir, in which case the cover 2 may be permanently secured to the body 1 by use of an adhesive, ultrasonic welding or any other method. It is to be understood that the medicament powder may consist purely of one or more active ingredients, or there may additionally be a carrier, for example lactose powder.

Extending laterally from the lower end of the main body portion 5 is an outlet 7, which, in the embodiment illustrated in FIG. 1 is in the form of a mouthpiece. If, however, the device were intended for nasal inhalation this would be replaced by a nosepiece. At its radially inner end the interior of the mouthpiece has a downwardly opening aperture 8 which communicates, as described below, with a dosing chamber containing a dose of powder to be inhaled. The outlet 7 is also provided with a pair of air inlets 9, one on each side, which allow the user to inhale additional air, and reduce the resistance to inhalation which the user experiences. It is understood that more air inlets could be provided on outlet 7 to allow more air into the outlet and to vary the air flow characteristics.

Figures 5, 6:
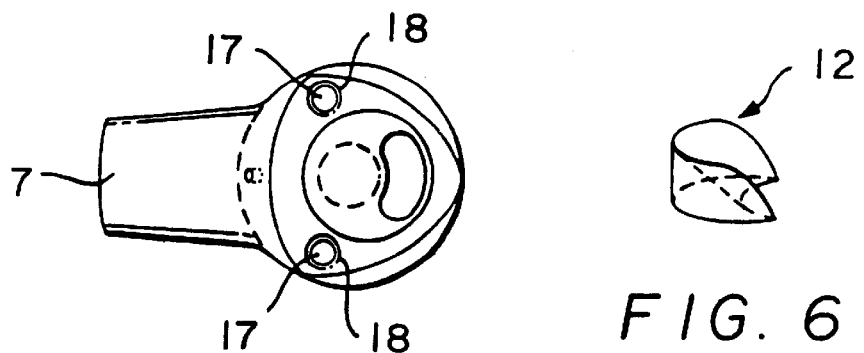
FIG. 5 is a plan view of the body.
FIG. 6 is a perspective view of a guide insert which is located inside the reservoir defined in the body.

The main body portion 5 has a base 10 in which is provided an arcuate aperture 11 through which powder can pass from the reservoir to the dosing member 3. The aperture 11 is surrounded by a wall 11a which extends downwardly from the base 10. Powder is guided to the aperture 11 by a guide insert 12, which is illustrated in FIG. 6. The guide insert 12 also serves to close off the reservoir from the interior of the outlet 7, so that powder cannot pass directly from the reservoir to the outlet.

A shaft 13, integral with the base 10 or fixedly secured thereto, extends downwardly therefrom. The shaft has a first portion 14 of larger diameter in which is formed a longitudinally extending slot 15, and a second portion 16 which is of smaller diameter and has a screwthreaded external surface. The base 10 is further provided with two lugs 30 arranged approximately equidistantly from one another and from the centre of the aperture 11, which extend downwardly from the base by an amount equal to the height of the wall 11a surrounding the aperture 11. The lugs 30 and wall 11a together define a planar surface for engagement by the upper surface of the dosing member 3.

The wall of the main body portion 5 of the body 1 is of sufficient thickness, at least in certain regions, to permit two longitudinal bores 18 to be formed therein. It is to be understood that instead of two bores, a single bore, or more than two bores, for example three bores, may be provided. An elongate weight 17 is slidably received in each of the bores. The weight is of a dense material, preferably metal, and one suitable material is stainless steel. An anvil 19 may be fixedly secured in the lower end of each bore. This is also preferably of metal, and brass has been found to be a suitable material. The upper end of each bore has a screwthreaded portion 20, which can receive a screw (not shown) used to secure the cover 2 to the body 1.

Figure 7:
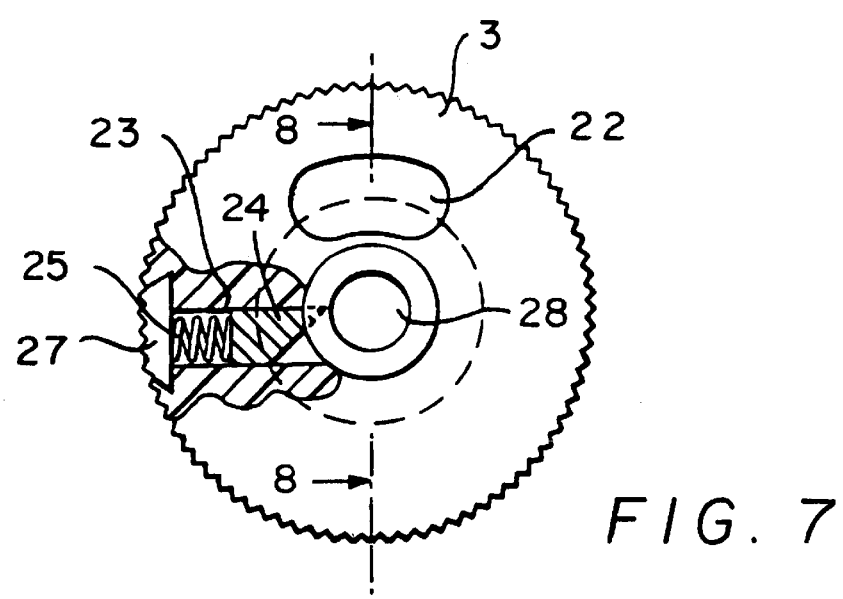
FIG. 7 is a plan view, partly cut away and on a larger scale, of a dosing member which forms part of the device of FIG. 1.
Figures 8, 9:
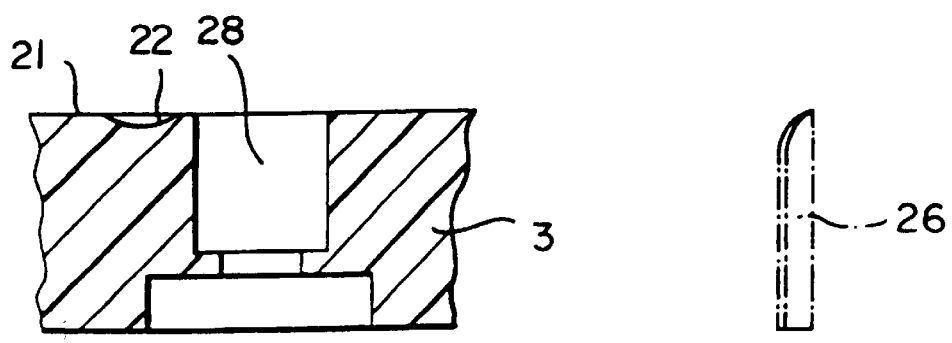
FIG. 8 is a partial section on line 8—8 in FIG. 7.
FIG. 9 shows a spring-retaining element which is inserted in the dosing member.

The dosing member 3 has an upper surface 21 in which is formed a metering recess 22. This has a volume equal to the volume of one dose of the powder in the reservoir. As seen in plan view, the recess 22 has a shape which is congruent to the aperture 11 in the base of the main body portion. As seen in section in FIG. 8, the recess has the form of shallow, arcuate depression with gently sloping sides. The advantages of this shape of recess will be explained below. It has been found that a recess capacity of between 5 mg and 26 mg of powder may be effectively employed. As shown in FIG. 7, the dosing member 3 has a nearly radial bore 23 in which a ratchet pawl 24 is slidably received. The pawl is urged inwardly by a spring 25 which is held in compression by a retaining element 26 received in a dovetail-shaped recess 27 in the periphery of the member 3. The inner end of the pawl 24 is urged against the portion 14 of the shaft 13. When the member 3 is in one particular position the pawl engages in the slot 15 in the portion 14. This is the position which is required during inhalation, as will be explained further below.

The dosing member 3 has a central opening 28 of stepped diameter, corresponding to the diameters of the portions 14 and 16 of the shaft 13, and is retained on the shaft by the nut 4 which engages the threaded surface of the shaft portion 16. A pharmaceutical grade rubber sealing ring or washer (not shown) may be incorporated in a groove around aperture 11 to prevent ingress of moisture between the body 1 and dosing member 3 into the reservoir 6. Such a sealing ring or washer may have a low friction coating such as polytetrafluoroethylene. The dosing member 3 has an indicator arrow 29 in its peripheral surface, and corresponding marks (not shown) are provided on the surface of the body 1, with which the user aligns the arrow at the various stages of operation of the device.

In operation, the user initially rotates the dosing member to the position in which the dosing recess is directly below the aperture 11, and thus in communication with the reservoir 6. The user then shakes the device in a generally upward and downward motion, while maintaining the device in a generally upright orientation. The weights 17 are thereby caused to travel up and down their respective bores 18. In so doing, the weights repeatedly strike against the anvils 19. The jolts which this produces cause the powder in the reservoir to be urged downwardly, and powder thus enters the metering recess 22. The jolts also have the effects of eliminating any bridging of powder, and ensuring that the powder is packed to a constant density. The latter point is important in ensuring uniform doses. What is desired is a uniform weight of powder, and the metering recess will not provide this unless the powder is of constant density. The shape of the metering recess 22 will have a direct effect on its filling characteristics. A shallow, arcuate depression will provide for rapid and complete filling of the recess with powder from the reservoir at substantially constant density throughout the recess.

The user then rotates the dosing member 3 through 180° to bring the recess 22 into alignment with the aperture 8 at the radially inner end of the outlet 7. The user knows when this position has been reached, as the pawl 24 is felt to engage with the slot 15. The user then inhales through the outlet 7, causing air to enter the outlet through the air inlets 9. The turbulent air flow created by the user inhaling through the outlet causes the powder in the recess 22 to be entrained in the airflow and inhaled by the patient. The shallow arcuate shape of the recess 22 allows for efficient entrainment of powder in the air flow. After inhalation, the user returns the dosing member to its initial position, ready for use again when required.

It will be appreciated by one skilled in the art that the size, number and configuration of the weights 17 in the device may be varied to provide optimum performance of the device depending on the size of the reservoir 6, the material from which the body 1 is moulded, its capacity to transmit vibrations, and the characteristics of the powder in the reservoir. For example, it has been found that positioning the bores 18 within the reservoir provides improved recess powder filling performance.

An alternative embodiment of the invention is shown in FIGS. 11 to 15. As in the embodiment shown in FIGS. 1 to 10, the embodiment of the device shown in cross section in FIGS. 11 and 12 comprises a main body portion 5 which defines a reservoir 6 and a reservoir cover or end cap 2. The reservoir 6 contains a supply of medicament in the form of a powder (not shown). The medicament may be as described above with reference to the embodiment shown in FIGS. 1 to 10.

The reservoir cover 2 may be provided with a desiccant cartridge (not shown) to absorb moisture and reduce the risk of the powder in the reservoir absorbing moisture and undergoing agglomeration of the particles thereof. The cover 2 may be removably secured to the body 5 by any known means, for example by means of a screw thread or a snap fit, to enable refilling of the reservoir 6 with powder. In this case a pharmaceutical grade rubber sealing ring 4 may be incorporated between the cover 2 and body 5 to prevent ingression of moisture into the reservoir 6. Alternatively, the device may be intended to be disposable after exhaustion of the supply of powder in the reservoir, in which case the cover 2 may be permanently secured to the body 5 by use of an adhesive, ultrasonic welding or any other method.

At its lower end the main body portion 5 is fitted with a base 10 which together with body 5 defines an aperture 11 which is offset from the vertical axis of the device and through which powder can pass from the reservoir to the dosing member 3. Powder is guided to the aperture by the walls of the reservoir which form a hopper. Extending laterally from the lower end of main body 5 is mouthpiece 7. If, however, the device were intended for nasal inhalation this would be replaced by a nosepiece. Dosing member 3 is mounted upon lower body portion 9 which is pivotally connected to main body 5 such that it may rotate about the vertical axis of the device. As explained in more detail below, lower body portion 9 serves to allow rotation of the dosing member 3 whilst maintaining the same in axial alignment with base 10. It also urges the dosing member 3 into close contact with base 10. Dust cover 33 is attached to lower body portion 9 through pivot 34.

A weight 31 in the form of a ring encircles the reservoir 6 and is slidable longitudinally thereof. The locus of movement of the weight 31 is defined towards the top of the reservoir by an end stop 32 formed as an integral part of the body 5, and towards the bottom of the reservoir by base 10 which behaves as an anvil. It is to be understood that whilst the device described herein incorporates a weight for the purpose described below, the weight is not an essential element of the invention and it might be chosen to omit the incorporation of the weight.

The lower face of base 10 is provided with a highly polished smooth and flat surface as is the contacting upper face of dosing member 3. These surfaces are ground and polished to render a surface finish giving a flatness which does not undulate over its area by more than 0.003 mm and a surface texture having a roughness average value (Ra) of 0.2 microns as internationally designated under ISO/R468, meaning that the average height of the irregularities constituting surface texture is 0.2 microns. These highly polished flat faces provide contacting surfaces between which there is substantially no clearance. It has been found that by providing such highly polished flat faces, the faces adhere to each other yet slide over each other as they are wrung together during assembly and use in the same way as mechanical slip gauges adhere to each other when wrung together. Air and powder are thus excluded from the interface between the base 10 and dosing member 3. When assembled the faces adhere firmly together but may be slid over each other without affecting the closeness of the interfacial contact. Such contacting surfaces have been found to provide excellent sealing characteristics both in the static state and during the sliding motion of one face over the other preventing both loss of powder from and ingression of moisture into the reservoir 6 through the interface between the base 10 and dosing member 3. This type of kinetic or sliding seal obviates the need for any additional sealing means between base 10 and dosing member 3. The contacting surfaces of base 10 and dosing member 3 are made of a hard rigid material, and suitable materials include acetal resins, ceramics and metals.

In the embodiment described, the two faces are formed by the surfaces of flat discs. It will be appreciated that disc shapes are not essential. Contact faces may be formed by the surfaces of a frusto-cone and a correspondingly frusto conical socket, by the contacting surfaces of two co-axial cylinders or by two correspondingly partially spherical contacting ball and socket surfaces.

Figure 13:
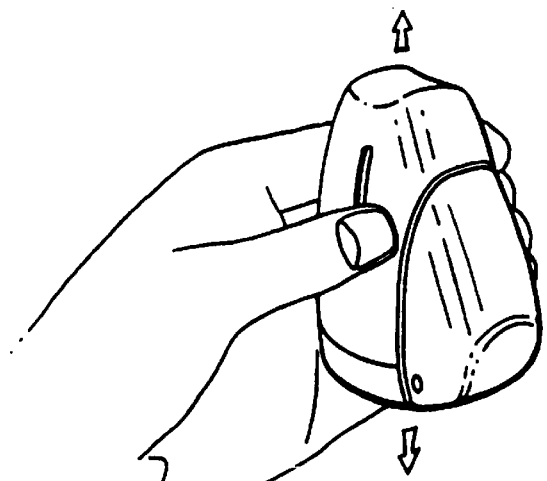
FIGS. 13 to 15 are perspective views showing three steps in the operation of the devices according to FIGS. 11, 12 and 16 to 19.

In operation, the user initially shakes the device in a generally upward and downward motion while maintaining the device in a generally upright orientation as shown in FIG. 13. Weight 31 is thereby caused to travel up and down the reservoir, so repeatedly striking end stop 32 and base 10. The jolts which this produces causes the powder in the reservoir to be urged downwardly and to enter the metering recess 22.

Figure 14:
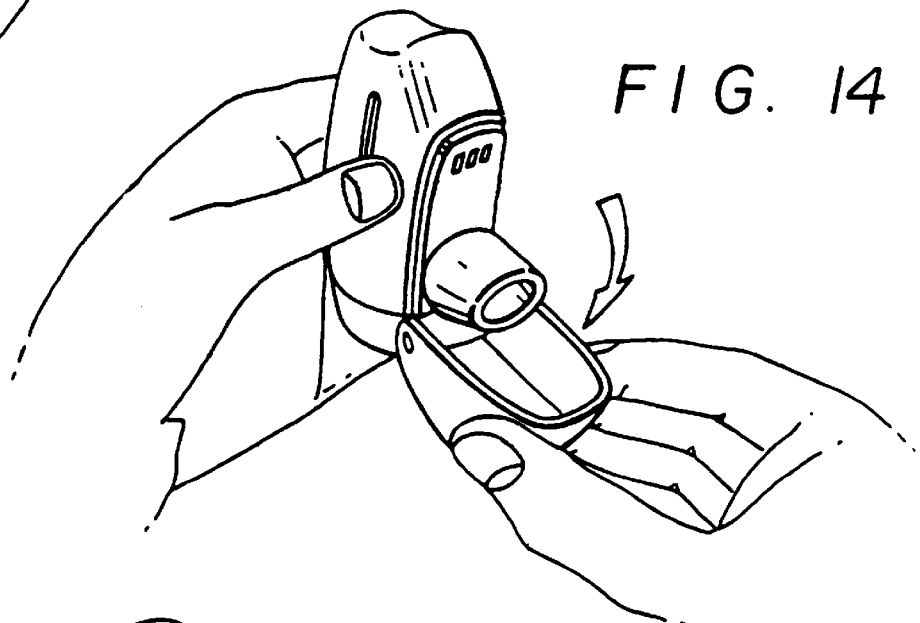
Figure 15:
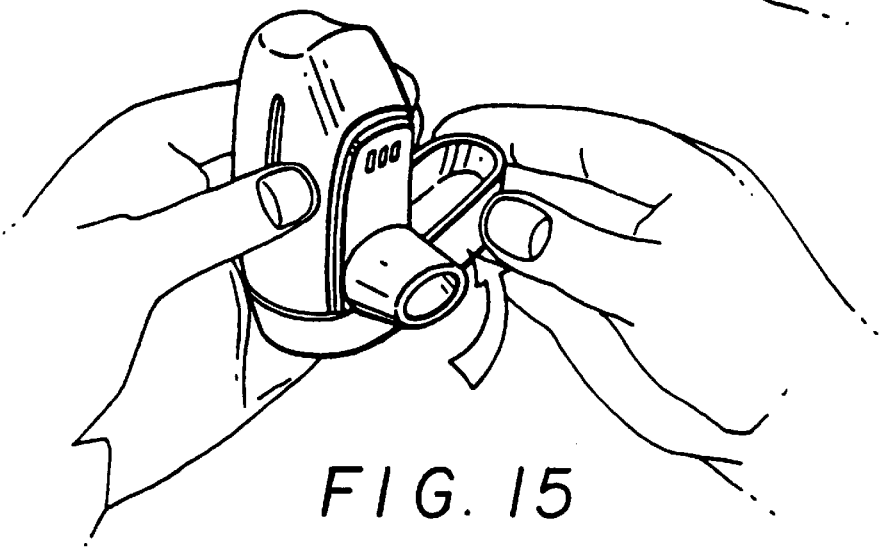

The user then opens dust cover 33, as shown in FIG. 14, and rotates the cover which is connected to lower body portion 9 as described above, through 90° as shown in FIG. 5, to move the dust cover 33 away from the mouthpiece 7 to allow access thereto and to bring the recess 22 into alignment with the aperture 8 leading to the mouthpiece 7 The user knows when this position has been reached as the lower body portion 9 engages a stop (not shown) and will not move any further. The user then inhales through mouthpiece 7. After inhalation the user returns the lower body portion 9 to its initial position and closes the dust cover 33.

In the device shown in FIGS. 11 and 12 the aperture 11 is radially offset by an angle of 90° about the vertical axis of the device from the aperture 8 at the inner end of the mouthpiece to allow the dust cover and lower body portion 9 to be moved through 90° for ease of access to the mouthpiece. However, it will be appreciated that this angle can be substantially increased or slightly decreased according to the desired angle of rotation of the dust cover, lower body portion and dosing member.

Further possible modifications to the device described include incorporation of a suitable dose counting mechanism to give the user an indication of the amount of powder remaining in the device.

A further embodiment of the invention is shown in FIGS. 16 to 19. As in the previous embodiments, the device shown in cross section in FIGS. 16 and 17 and in exploded view in FIG. 18 comprises an elongate main body portion 55 which defines a reservoir 56 and a reservoir cover or end cap 52. The reservoir 56 contains a supply of medicament in the form of a powder (not shown). The reservoir cover 52 is secured to the body 55 by a snap fit and a pharmaceutical grade rubber sealing ring 54 is incorporated between the cover 52 and body 55 to prevent ingression of moisture into the reservoir 56.

At its lower end the main body portion 55 is fitted with a base member 60 which together with body 55 defines an aperture 51 which is offset from the vertical axis of the device and through which powder can pass from the reservoir to a recess 65 in dosing member 53. The lower face of base member 60 is provided with a similarly highly polished smooth and flat surface to that described with reference to the embodiment shown in FIGS. 11 to 15 as is the upper face of dosing member 53. Powder is guided to the aperture by the walls of the reservoir which form a hopper. Extending laterally from the lower end of the main body 55 is mouthpiece 57. Dosing member 53 is mounted upon lower body assembly 59 which is pivotally connected to main body 55 such that it may rotate about the vertical axis of the device. Lower body assembly 59 serves to transmit rotational movement thereof to the dosing member 53 whilst maintaining the same in axial alignment with base member 60. It also urges dosing member 53 into close contact with base 60 by means of spring 61. Dust cover 63 (not shown in FIGS. 16 and 17) is attached to lower body portion 69 through pivot 64.

The wall of the main body 55 is provided with three longitudinal bores 58 substantially equidistantly spaced around the reservoir 56. A cylindrical weight 67 is slideably received in each of the bores 58. The weights 67 may be made of a rust resistant metal such as stainless steel or other hard material such as acetal resin. The bores are each blind at their upper ends and closed by a pressed-in stainless steel ball bearing 68 at their lower ends which also act as anvils against which weights 67 may impact as described later.

A dose indicator drive means comprising a shaft 70 provided with a screw thread over much of its length, a sprung lug 71 at the base of the thread and a sprocket 72 with inclined teeth positioned below the lug is rotatably mounted within a bore 73 in the wall of the main body 55 (see FIG. 19). An indicator nut 77 is threaded into the shaft with a projection protruding through an indicator window 74 in the wall of bore 73 which prevents the indicator nut 77 from rotating with shaft 70. Sprung lug 71 engages with teeth 75 formed within bore 73 to form a ratchet allowing shaft 70 to rotate in one direction only. Sprocket 72 is located adjacent the periphery of dosing member 53 which is provided with a second sprung lug 76.

Operation of the device is similar to that described with reference to the embodiment shown in FIGS. 11 to 15. The user initially shakes the device in a generally upward and downward motion while maintaining the device in a generally upright orientation as shown in FIG. 13. Weights 67 are thereby caused to travel up and down bores 58 next to the reservoir, so repeatedly striking anvils 68. The vibrations which this produces are transmitted through base member 60 and body 55 to the powder in the reservoir, and this encourages powder to flow downwardly and enter metering recess 65 within dosing member 53.

The user then opens dust cover 63, as shown in FIG. 14, and rotates the cover which is connected to lower body assembly 59 as described above through 90° as shown in FIG. 5, to move dust cover 63 away from mouthpiece 57 to allow access thereto and to bring recess 65 into alignment with the aperture at 66 leading to the mouthpiece 57. As the dosing member 53 rotates with the lower body assembly 59, lug 76 engages an inclined tooth presented by sprocket 72 of the dose indicator drive means. The dose indicator drive means is prevented from turning in the direction urged by lug 76 by virtue of the ratchet mechanism formed by teeth 75 and lug 71. As a result, lug 76 rides over the inclined tooth and out of engagement with sprocket 72. The lower body assembly 59 engages a stop (not shown) and will not move any further when the recess 65 is correctly aligned with aperture 66.

The user now inhales through mouthpiece 57. Air is drawn through grill 80 and passage 81, defined by body 55 and hole 82 in base member 60, and entrains the powder in recess 65 of dosing member 53. The airflow draws the entrained powder through the mouthpiece 57 and is inhaled by the user. Further air is drawn into the mouthpiece through holes 82 on either side of mouthpiece 57 and this creates turbulence which helps to break-up any agglomerates of powder entrained.

After inhalation the user returns lower body assembly 59 to its initial position and closes the dust cover 63. As dosing member 53 rotates, lug 76 again engages sprocket 72 of the dose indicator drive means. As the ratchet mechanism formed by teeth 75 and lug 71 allows movement of the dose indicator drive means in the direction as now urged by lug 76, the dose indicator drive means is rotated by one tooth pitch through engagement with lug 76 as it passes sprocket 72. Rotation of the dose indicatior drive means causes the captive dose indictor nut 73 to travel down threaded shaft 70. The pitch of the thread and the number of teeth on sprocket 72 are selected to ensure that the dose indicator nut travels from the uppermost "full" position to the lowermost "empty" position when the device has been used sufficiently to deliver its prescribed number of doses, so indicting to the user that the device is empty.

It will be understood that the present disclosure is for the purpose of illustration only and the invention extends to modifications, variations and improvements thereto.

What is clamed is:

1. An inhalation device comprising a body forming a reservoir for medicaments in the form of a powder, an outlet through which a user can inhale, and a dosing member with at least one metering recess formed therein, the dosing member being movable between a position in which the at least one metering recess communicates with the reservoir to receive a dose of powder therefrom and a position in which the at least one metering recess communicates with the outlet to permit the user to inhale the dose, the at least one metering recess being formed in a face of the dosing member, the face being mounted in contact against a similar mating face of the body, characterised in that the face of the dosing member and the said mating face of the body have highly polished smooth surfaces which form a contacting face to face seal in which said sealing faces adhere to each other sufficiently to exclude air and moisture while being slidable relative to each other.

2. A device according to claim 1, characterised in that the sealing faces have a surface texture sufficiently smooth to have a roughness average value (Ra) of 0.5 microns or less.

3. A device according to claim 2, characterised in that the sealing faces have a surface texture sufficiently smooth to have an Ra value of 0.2 microns or less.

4. A device according to claim 1, characterised in that the sealing faces are flat.

5. A device according to claim 4, characterised in that the sealing faces have a flatness of 0.005 mm or less.

6. A device according to claim 5, characterised in that the sealing faces have a flatness of 0.003 mm or less.

7. A device according to claim 1, characterised in that the sealing faces are cylindrical.

8. A device according to claim 1, characterised in that the sealing faces are disc shaped.

9. A device according to claim 1, characterised in that the sealing faces are made of a hard rigid material.

10. A device according to claim 9, characterised in that the sealing faces are made of acetal resin.

11. A device according to claim 9, characterised in that the sealing faces are made of ceramics.

12. A device according to claim 9, characterised in that the sealing faces are made of metal.

13. A device according to claim 1, further comprising a dose indicating means adapted to display to a user the quantity of medicament remaining within the reservoir.

14. A device according to claim 1, characterised in that the sealing faces are highly polished surfaces made of a hard rigid material.

15. A device according to claim 1, characterised in that the sealing faces are highly polished metal surfaces.

16. An inhalation device comprising a body defining a reservoir for medicaments in the form of a powder, an outlet through which a user can inhale and a dosing member with at least one metering recess formed therein, the dosing member being movable between a position in which the at least one metering recess communicates with the reservoir to receive a dose of powder therefrom and a position in which the at least one metering recess communicates with the outlet to permit the user to inhale the dose, the at least one metering recess being formed in a face of the dosing member, the face being mounted in contact against a similar mating face of the body at the lower end of the reservoir, characterised in that the face of the dosing member and the mating face of the body are sealing faces with highly polished surfaces which adhere to each other sufficiently to exclude air and moisture while being slidable relative to each other.

17. A device according to claim 16, characterised in that the sealing faces have a surface texture sufficiently smooth to have a roughness average value (Ra) of 0.5 microns or less.

18. A device according to claim 17, characterised in that the sealing faces have a surface texture sufficiently smooth to have an Ra value of 0.2 microns or less.

19. A device according to claim 16, characterised in that the sealing faces are flat.

20. A device according to claim 19, characterised in that the sealing faces have a flatness of 0.005 mm or less.

21. A device according to claim 20, characterised in that the sealing faces have a flatness of 0.003 mm or less.

22. A device according to claim 16, characterised in that the sealing faces are cylindrical.

23. A device according to claim 16, characterised in that the sealing faces are disc shaped.

24. A device according to claim 16, characterised in that the sealing faces are made of a hard rigid material.

25. A device according to claim 24, characterised in that the sealing faces are made of acetal resin.

26. A device according to claim 24, characterised in that the sealing faces are made of ceramics.

27. A device according to claim 24, characterised in that the sealing faces are made of metal.

28. A device according to claim 16, further comprising a dose indicating means adapted to display to a user the quantity of medicament remaining within the reservoir.

29. A device according to claim 16, characterised in that the sealing faces are highly polished surfaces made of a hard rigid material.

30. A device according to claim 16, characterised in that the sealing faces are highly polished metal surfaces.

* * * * *